United States Patent [19]

Cormier

[11] 4,443,446

[45] Apr. 17, 1984

[54] USE OF PSYCHOACTIVE DRUGS AS VAGINAL CONTRACEPTIVES

[75] Inventor: Milton J. Cormier, Bogart, Ga.

[73] Assignee: University of Georgia Research Foundation, Inc., Athens, Ga.

[21] Appl. No.: 155,800

[22] Filed: May 30, 1980

[51] Int. Cl.$^3$ .................. A61K 31/38; A61K 31/54; A61K 31/445

[52] U.S. Cl. .................................. 424/247; 424/244; 424/250; 424/267; 424/275; 424/330; 424/331; 424/DIG. 14

[58] Field of Search ............... 424/DIG. 14, 244, 247, 424/250, 267, 275, 330, 331

[56] References Cited

U.S. PATENT DOCUMENTS 2,541,103  2/1951  Sander .................. 424/DIG. 14

OTHER PUBLICATIONS

Mann, Thaddeus, *The Biochemistry of Semen and of the Male Reproductive Tract*, John Wiley & Sons, 1964, pp. 391–392.
Mann, Thaddeus, *The Biochemistry of Semen*, John Wiley & Sons, 1954, pp. 54–55.
Chemical Abstracts, 82:11065u, (1975).
Chemical Abstracts, 82:25709u, (1975).
Chemical Abstracts, 72:130759b, (1970).
Physicians Desk Reference (PDR), 26th Ed., 1972, pp. 909, 910.

*Primary Examiner*—Leonard Schenkman
*Attorney, Agent, or Firm*—Sumner C. Rosenberg

[57] ABSTRACT

The use of psychoactive drugs as vaginal contraceptives is disclosed. The invention may be implemented by incorporating a psychoactive drug in a known method such as jelly, foam, or suppository introduction means prior to intercourse. Furthermore, the use of psychoactive drugs after intercourse using the above methods is disclosed.

10 Claims, No Drawings

USE OF PSYCHOACTIVE DRUGS AS VAGINAL CONTRACEPTIVES

The present invention relates to a method of preventing conception. More specifically, the present invention relates to the use of psychoactive drugs as vaginal contraceptives.

Presently, many forms of contraception are available, including oral contraceptives, mechanical contraceptives, and vaginal contraceptive solutions generally comprising spermatocides. Each form of contraception suffers from undesirable characteristics such as varying effectiveness, discomfort, or physical side effects.

Vaginal contraceptives comprising spermatocidal agents are well known in the prior art in many methods of usage, including jellies and creams (hereinafter referred to as jelly), foams from tablets or aerosols, and suppositories. However, these methods are among the least effective in terms of preventing conception and are basically unsatisfactory as a sole method of contraception.

Psychoactive drugs are currently used clinically to treat certain types of mental disorders and stress. Chemical classes of psychoactive drugs and examples of drugs in each class are as follows:

| Chemical Class | Examples |
| --- | --- |
| Phenothiazines | Trifluoperazine |
|  | Fluphenazine |
|  | Thioridazine |
|  | Chlorpromazine |
|  | Promethazine |
| Thioxanthenes | Chlorprothixene |
| Butyrophenones | Penfluridol |
|  | Benperidol |
|  | Haloperidol |
| Diphenylbutylamines | Pimozide |
| Dibenzodiazepines | Clozapine |
| Benzodiazepines | Medazepam |
|  | Chlordiazepoxide |
| Dibenzazepines | Imipramine |
|  | Amitriptyline |
|  | Protriptyline |
|  | Desipramine |

The use of psychoactive drugs as medications to affect mental processes has become widespread since the early 1950's. Such use typically entails taking such drugs internally at dosages ranging from 10 to 120 milligrams daily. For a detailed background of such use and description of such drugs see Chapter 12 of *The Pharmacological Basis of Theraputics*, 5th Ed., edited by L. S. Goodman and A. Gilman (1975).

DESCRIPTION OF THE INVENTION

The present invention comprises the use of an effective psychoactive drug as vaginal contraceptive. The introduction of such drugs into the vagina can be accomplished by any of the many commonly available methods currently used in conjunction with spermatocides, such as jelly, foam or suppository means. By substitution of the appropriate amount or concentration of an effective psychoactive drug in place of, or in addition to, the spermatocidal agent in any of these means, a form of contraceptive embodying the invention, to be applied in the same manner prior to sexual intercourse, is accomplished. The present invention also comprises the use of an effective psychoactive drug shortly after intercourse to prevent conception. This may be accomplished by use of a suppository, jelly or other suitable vehicle containing the appropriate amount of an effective psychoactive drug.

As stated previously, current forms of vaginal contraceptives are based on the use of spermatocides, which are intended to kill the sperm. Generally, the use of such contraceptives by themselves have not proven to be a satisfactorily effective contraceptive method. The present invention does not involve the killing of the sperm, but instead directly and specifically blocks the physiological process of conception and results in greatly improved effectiveness of contraception.

It has been shown in the past few years that there is a regulatory protein known as calmodulin, found in all cells of higher organisms and which is the key to the control of a wide variety of physiological processes. We have found that calmodulin is involved in triggering the activation of mammalian spermatoza, a prerequisite to the fertilization process. Calmodulin is a calcium binding protein, which means that when calcium is bound to the protein the resulting calcium-protein complex turns on a variety of cellular processes including spermatozoan activation.

It is known tht psychoactive drugs will bind tightly to calmodulin only in the presence of calcium. The binding of these drugs to calmodulin results in the inhibition of calmodulin function. We have found that of the many thousands of proteins found in a cell, calmodulin is the only detectable target of psychoactive drugs. Thus, psychoactive drugs are specific in their binding to calmodulin and will specifically inhibit calmodulin function.

The use of an effective psychoactive drug as a vaginal contraceptive has a number of advantages. First, it is extremely effective since the specific binding of the drug to calmodulin would turn off spermatozoan activation and thus prevent fertilization. Experimental evidence has demonstrated that the phenothiazine drugs penetrate the spermatozoan membranes within seconds and concentrate in the region of the cell occupied by calmodulin. Second, there will be no expected side effects since the drug would not be used internally and since low concentrations will be very effective as a vaginal contraceptive. Third, the effectiveness of an application may last for hours due to the stability of these drugs.

Additionally, evidence has indicted that calmodulin is also the target protein during ovum activation since this is also a calcium dependent process. Thus if the drug comes into contact with the ovum, fertilization will not occur. It is seen, therefore, that the present invention may be doubly effective by preventing activation of both the sperm and the egg.

The most promising specific drugs, in order of effectiveness, are: penfluridol, pimozide, trifluoperazine, chlorprothixene, thioridazine, chlorpromazine, benperidol, haloperidol, and clozapine. While a concentration of 0.5% (5 milligrams per milliliter of jelly) will be effective in the most effective drugs such as penfluridol or trifluoperazine, less effective drugs will require a higher concentration to achieve similar effectiveness.

A preferred embodiment of the present invention comprises a one-half percent concentration of trifluoperazine in a jelly, introduced into the vagina in sufficient quantity and under known methods prior to sexual intercourse and allowed to remain therein for a period of time, preferably more than a few hours, after intercourse.

What is claimed is:

1. A method for preventing conception in a female which comprises: introducing an effective amount of a calmodulin binding psychoactive drug selected from the group consisting of penfluridol, pimozide, trifluoperazine, chlorpromazine, benperidol, haloperidol, and clozapine into the vagina of the female.

2. The method as described in claim 1 wherein the introduction of said pschoactive drug comprises the steps of: introducing said psychoactive drug into the vagina of the female prior to sexual intercourse; and allowing said psychoactive drug to remain in the vagina during and after sexual intercourse.

3. The method described in claim 2, wherein the step of introducing said psychoactive drug comprises introducing a mixture of said psychoactive drug and a foam carrier into the vagina of the female prior to sexual intercourse by foam injection means.

4. The method as described in claim 2, wherein the step of introducing said psychoactive drug comprises introducing a mixture of said psychoactive drug and a jelly carrier into the vagina of the female prior to sexual intercourse by jelly insertion means.

5. The method as described in claim 2, wherein said psychoactive drug is introduced into the vagina of the female by suppository means.

6. The method as described in claim 1 wherein the introduction of said psychoactive drug comprises: introducing said psychoactive drug into the vagina after sexual intercourse.

7. The method as described in claim 6, wherein the step of introducing said psychoactive drug comprises introducing a mixture of said psychoactive drug and a suitable carrier into the vagina.

8. The method as described by claims 1, 2, 3, 4, 5, 6, or 7, wherein the amount of the psychoactive drug introduced into the vagina is about 10 milligrams or greater.

9. A contraceptive composition comprising an effective amount of a psychoactive drug selected from the group consisting of penfluridol, pimozide, trifluoperazine, chlorprothixene, thioridazine, chlorpromazine, benperidol, haloperidol, and clozapine; and a suitable vaginal carrier medium selected from the group consisting of jelly carriers, foam carriers and suppository carriers.

10. The composition as described in claim 9, wherein the concentration of said psychoactive drug is equal to or greater than 5 milligrams per milliliter of said carrier medium.

* * * * *